United States Patent [19]

Ogata et al.

[11] 4,182,621
[45] Jan. 8, 1980

[54] COMPOSITION FOR INHIBITING THE GROWTH OF PLANTS

[75] Inventors: Yuzuru Ogata; Toshio Fukuhara, both of Tokushima; Shigeru Araki, Naruto, all of Japan

[73] Assignee: Otsuka Kagaku Yakuhin Kabushiki Kaisha, Bungomachi, Japan

[21] Appl. No.: 909,524

[22] Filed: May 25, 1978

[30] Foreign Application Priority Data

Feb. 1, 1978 [JP] Japan .................. 53-10874
May 12, 1978 [JP] Japan .................. 53-57011

[51] Int. Cl.² .................. A01N 5/00; A01N 9/22
[52] U.S. Cl. .................. 71/76; 71/78; 71/92; 71/97; 71/103; 71/113; 71/115; 71/124; 71/DIG. 1
[58] Field of Search .................. 71/76, 78, 92, DIG. 1, 71/103

[56] References Cited

U.S. PATENT DOCUMENTS

| | | | |
|---|---|---|---|
| 2,614,916 | 10/1952 | Hoffmann et al. ............ | 71/92 |
| 2,805,926 | 9/1957 | Schoene et al. ............ | 71/92 |
| 3,503,729 | 3/1970 | Corkins ............ | 71/92 |
| 3,556,763 | 1/1971 | Gower et al. ............ | 71/78 |
| 3,697,250 | 10/1952 | Young et al. ............ | 71/78 |
| 3,713,804 | 1/1973 | Moccia ............ | 71/DIG. 1 |
| 3,954,439 | 5/1976 | Papamichael et al. ............ | 71/DIG. 1 |
| 3,990,884 | 11/1976 | Barker ............ | 71/DIG. 1 |

FOREIGN PATENT DOCUMENTS

| | | | |
|---|---|---|---|
| 46-22234 | 6/1971 | Japan ............ | 71/DIG. 1 |
| 52-87231 | 7/1977 | Japan ............ | 71/DIG. 1 |
| 719445 | 12/1954 | United Kingdom ............ | 71/DIG. 1 |

*Primary Examiner*—Glennon H. Hollrah
*Attorney, Agent, or Firm*—Armstrong, Nikaido, Marmelstein & Kubovcik

[57] ABSTRACT

A composition for inhibiting the growth of plants comprising:
(1) 6-hydroxy-3-(2H)-pyridazinone or a salt thereof,
(2) at least one compound represented by the formula

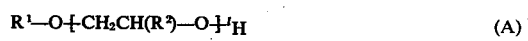 (A)

wherein $R^1$ is alkyl, alkenyl, aralkyl, alkylphenyl or alkylnaphthyl group, $R^2$ is H or $-CH_3$, $l$ is an integer of 3 to 30, and
(3) at least one compound represented by the formula

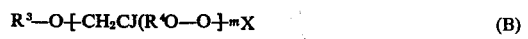 (B)

wherein $R^3$ is alkyl, alkenyl, aralkyl, alkylphenyl or alkylnaphthyl group, $R^4$ is H or $CH_3$, m is an integer of 1 to 100, X is $-SO_3M$, $-CH_2CH(OH)CH_2SO_3M$, $-CH_2CH_2SO_3M$, $-CH_2CH_2CH_2SO_3M$, $-CH_2CH_2CH_2CH_2SO_3M$, $-OCH_2COOM$, $-OCH_2CH_2COOM$ or $-OCH_2CH(CH_3)COOM$, M being alkali metal, alkaline earth metal, ammonium group, quaternary ammonium group or H.

6 Claims, No Drawings

COMPOSITION FOR INHIBITING THE GROWTH OF PLANTS

This invention relates to novel and improved compositions for inhibiting the growth of plants comprising 6-hydroxy-3-(2H)-pyridazinone (hereinafter referred to as "HP") or a salt thereof, and more particularly to plant growth inhibitors comprising HP or a salt thereof and auxiliary agents.

HP and salts thereof which have activity to inhibit the growth of plants are widely used for example for controlling weeds and inhibiting the growth of lateral buds of tobacco plants. However, the results achieved by these compounds as tested by experiments and used in the field reveal that the growth inhibiting activity of the compounds is dependent heavily on the conditions under which they are applied. For example, the inhibiting activity varies greatly under conditions which involve a relative humidity of lower than 70% and/or in which plants are under stress due to a deficiency of water. Further even under ideal conditions in which plants can be grown at a high humidity, the HP efficiency (i.e. the ratio of the amount of HP which must be present in the cells of meristematic tissue for the inhibition of growth to the amount of HP which must be applied to the plant to produce activity on the plant) is very low as is well known. Thus the conditions surrounding the plant govern the effectiveness of HP or salt thereof, namely the penetration of the compound into the body of the plant and the migration of the compound to the site of growth. It is therefore extremely difficult to apply HP or salt thereof in a proper amount.

To overcome this problem, it is known to use, in combination with HP or its salt, an auxiliary agent containing a branched aliphatic portion having a hydroxyl group at its one end and linked at the other end thereof to a polyoxyethylene chain through an intervening oxygen atom (Japanese Patent Publication No. 22234/1971) or a polyoxyethylene alkylphenyl ether serving as an auxiliary agent (Japanese Patent Application Disclosure No. 87231/1977).

The known method contemplates a reduction in the surface tension of the solution of HP or salt thereof to cause the compound to more effectively spread on and penetrate into the plant treated therewith. Accordingly the method requires the use of a nonionic surfactant of low HLB for imparting reduced surface tension. However, it is sometimes impossible to dissolve such surfactant directly into a concentrated solution of HP or its salt, although it is desirable for the convenience of transport and handling to prepare a concentrated preparation which will be diluted to a specified concentration immediately before use. Consequently there arises the necessity of preparing a solution of HP or salt thereof and another solution of a nonionic surfactant, each in a specified concentration, and mixing the solutions together for application to plants. This involves a cumbersome procedure. In some cases, moreover, an organic solvent may have to be used. The preparation thus obtained is very inconvenient to handle for dealers as well as for users. Additionally HP or salts thereof per se still remain to be improved in their inhibitory effects on the growth of plants.

An object of this invention is to provide compositions having a steady inhibiting activity on the growth of plants without being influenced by the environmental conditions of the plant.

Another object of this invention is to provide compositions for inhibiting the growth of plants which are in the form of a single solution comprising HP or a salt thereof and auxiliary agents and which are usable free of the inconvenience to be experienced when the active component and the auxiliary agents are prepared as individual solutions to be mixed together for application.

Another object of this invention is to provide plant growth inhibitors of the single solution type containing no organic solvent.

Another object of this invention is to provide compositions having a greatly improved inhibiting activity on the growth of plants as compared with conventional plant growth inhibitors consisting essentially of HP or a salt thereof or comprising such an active ingredient and an auxiliary agent.

These and other objects and features of this invention will become apparent from the following description.

To fulfil the foregoing objects, this invention provides a composition comprising at least one of HP and salts thereof, at least one compound represented by the formula (A)

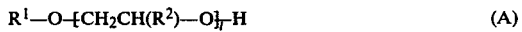

$$R^1-O+CH_2CH(R^2)-O]_l-H \qquad (A)$$

wherein $R^1$ is alkyl, alkenyl, aralkyl, alkylphenyl or alkylnaphthyl group, $R^2$ is H or $CH_3$ and $l$ is an integer of from 3 to 30, and at least one compound represented by the formula (B)

$$R^3-O+CH_2CH(R^4)-O]_m X \qquad (B)$$

wherein $R^3$ is alkyl, alkenyl, aralkyl, alkylphenyl or alkylnaphthyl group, $R^4$ is H or $CH_3$, m is an integer of from 1 to 100, and X is $-SO_3M$, $-CH_2CH(OH)CH_2SO_3M$, $-CH_2CH_2SO_3M$, $-CH_2CH_2CH_2SO_3M$, $-CH_2CH_2CH_2CH_2SO_3M$, $-OCH_2COOM$, $-OCH_2CH_2COOM$ or $-OCH_2CH(CH_3)COOM$, M being alkali metal, alkaline earth metal, ammonium group, quaternary ammonium group or H.

Thus the composition of this invention comprises HP and/or a salt thereof having activity to inhibit the growth of plants, a compound of the formula (A) and a compound of the formula (B). With the use of the two kinds of specific compounds in combination with the active component, the three components act synergically, giving a greatly increased activity to inhibit the growth of plants. The use of the compounds also results in the advantages that an aqueous solution of HP or a salt thereof can be prepared in a desired concentration and that the solution obtained has a high cloud point and improved stability at high temperatures as well as at low temperatures.

According to this invention, at least one of HP and various salts thereof is used as the active component. Examples of useful HP salts are salts of alkali metals, ammonia, primary amines, secondary amines and tertiary amines, quaternary ammonium salts, basic salts of amino acids, water-soluble salts of polyvalent metals, etc. Examples of especially preferable salts are salts of potassium and sodium, and salts of ethanolamine, diethanolamine, triethanolamine, lysine, histidine and choline. Examples of useful water-soluble salts of polyvalent metals are salts of metals such as copper, zinc, calcium, barium, magnesium and iron.

The compounds of the formula (A) useful as one of the auxiliary agents are commercially available as nonionic surfactants and are polyoxyethylene ether and/or polyoxypropylene ether compounds having $C_6$-$C_{12}$ straight chain or branched chain alkyl group, alkenyl group such as vinyl ($CH_2=CH-$), allyl ($CH_2=CH-CH_2-$), propynyl ($CH\equiv C-CH_2$) or ethynyl ($CH\equiv C-$) group, aralkyl group such as phenethyl group

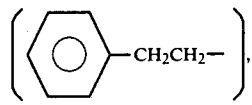

alkylphenyl group having $C_6$-$C_{15}$ alkyl group of alkylnaphthyl group having $C_8$-$C_{18}$ alkyl group as $R^1$. These compounds are prepared by polymerizing a $C_6$-$C_{18}$, preferably $C_8$-$C_{18}$, higher alcohol having a straight chain or branched chain, alkylphenol, alkylnaphthol and/or styrenated phenol with 3 to 30 moles, preferably 6 to 20 moles or ethylene oxide or propylene oxide per mole of the former by addition condensation. Also usable are compounds prepared by polymerizing such alcohol and/or alkylphenol with ethylene oxide and propylene oxide alternately or randomly by addition condensation. Examples of such compounds are polyoxyethylene(8)dodecyl ether, polyoxyethylene(20)dodecyl ether, polyoxyethylene(10)trimethylnonyl ether, polyoxyethylene(14)trimethylheptyl ether, polyoxyethylene(8)trimethylbutyl ether, polyoxyethylene(8)oleyl ether, polyoxyethylene(15)diethylhexyl ether, polyoxyethylene(6)nonylphenyl ether, polyoxyethylene(9)nonylphenyl ether, polyoxyethylene(11)nonylphenyl ether, polyoxyethylene(20)nonylphenyl ether, polyoxyethylene(10)octylphenyl ether, polyoxyethylene(10)tridecylphenyl ether, polyoxyethylene(10)octylnaphthyl ether, polyoxypropylene(10)octylnaphthyl ether, polyoxypropylene(10)laurylnaphthyl ether, etc. (The number in each pair of the parentheses represents the mole number of oxyethylene chains.)

The compounds of the formula (B) are prepared by introducing a sulfuric acid group, sulfo group or carboxyl group into the corresponding commercially available nonionic surfactants by a known method. The nonionic surfactants include those represented by the formula (A) and also those prepared by the addition condensation polymerization of ethylene oxide or propylene oxide and containing 1 to 100 moles, preferably 3 to 80 moles of the alkylene oxide. Examples of compounds of the formula (B) are polyoxyethylene(50)trimethylbutyl ether sodium sulfate, polyoxyethylene(75)trimethylnonyl ether sodium sulfate, polyoxyethylene(4)diethylhexyl ether sodium sulfate, polyoxyethylene(25)tridecylphenyl ether sodium sulfate, polyoxyethylene(25)octylnaphthyl ether sodium sulfate, polyoxypropylene(25)laurylnaphthyl ether sodium sulfate, etc. Representative examples of compounds of the formula are those commercially available such as "Levenol WZ", "Latemul WX", "Emal 20 C", (trade mark, Japan, products of Kao-Atlas Co., Ltd.), "Newcol 560 SN", "Newcol 861 S", "Newcol 1305 SN" (trade mark, Japan, products of Nihon Nyukazai Co., Ltd.).

The compositions of this invention are used as diluted to aqueous solutions of suitable concentration or as supported on solid particles as of silicate. Examples of useful carriers are mica, talc, clay, agalmatolite, etc.

The present compositions are applicable to plants by various methods as by spraying, dusting, or brushing. Preferably the compositions are used in the form of a dilute aqueous solution or suspension. To achieve satisfactory growth inhibiting effects, the solution or suspension should contain 0.1 to 1% by weight, preferably 0.2 to 0.6% by weight of HP or salt thereof based on the solution or suspension.

The compound of the formula (A) is incorporated in the compositions of this invention in such an amount that the concentration of the compound in the composition to be actually applied to plants is not lower than the critical micelle concentration (CMC) thereof. Thus usually 0.001 to 1.5 parts by weight, preferably 0.003 to 1 part by weight, of the compound of the formula (A) is used per part by weight of HP or salt thereof. The compound of the formula (B) is used in an amount of about 1 to about 1,000% by weight, preferably about 20 to about 500% by weight, based on the compound of the formula (A).

The use of the two compounds of the formulae (A) and (B) conjointly with the active component according to this invention enables the three components to produce an outstanding synergic effect for reasons which still remain to be fully clarified. The compound of the formula (B) is inferior to the compound of the formula (A) in surface tension reducing activity and is higher than the latter in CMC, so that the former must be used in a greater amount than the latter. It is therefore thought that the compound of the formula (B) is considerably inferior to that of the formula (A) in growth inhibiting activity. On the other hand, the compound of the formula (A) inherently has a high surface-active ability and is effective in reducing the surface tension of the aqueous solution of HP or salt thereof to enable the solution to penetrate into the plant body. However, this compound will not have an especially great effect to cause the taken-in HP or salt thereof to migrate into the meristematic tissue where the growth of the plant is to be inhibited. Nevertheless, it appears that the two compounds, when used together, act favorably on each other in one way or another and eventually produce a remarkably improved growth inhibiting effect.

The compositions of this invention have the following advantages.

1. The present compositions have especially high stability at low temperatures as well as at high temperatures, are therefore preservable for a prolonged period of time in any season and are convenient to use because they are applicable to plants when merely diluted to a specified concentration immediately before use.

2. The present compositions have an exceedingly higher growth inhibiting activity than conventional inhibitors. When various inhibitors were tested for activity to inhibit the growth of lateral buds on tobacco plants within a greenhouse using pots, the inhibition ratio achieved was 78.3% with 0.08% of diethanolamine salt of HP, 25.4% with 0.16% of potassium salt of HP, and 74.3% with the conjoint use of 0.08% of potassium salt of HP and 0.1% of polyoxyethylene(10)trimethylnonyl ether, whereas for example an inhibition ratio of 98.9% was achieved with a composition of this invention composed of 0.08% of potassium salt of HP, 0.08% of polyoxyethylene(10)trimethylnonyl ether and 0.02% of sodium sulfate of polyoxyethylene(75)nonylphenyl ether. Various inhibitors were applied to tobacco plants also in the field and the lateral buds on tobacco were collected on the 14th day thereafter. The weight of the buds per plant was 2.5 g with 0.5% of diethanolamine salt of HP, 5.8 g with the conjoint use of 0.3% of potassium salt of HP and 0.15% of polyoxyethylene(10)trimethylnonyl ether, and 1.5 g with a composition of this invention composed of 0.3% of potassium salt of HP, 0.05% of polyoxyethylene(10)trimethylnonyl ether and 0.05% of sodium sulfate of polyoxyethylene(75)nonylphenyl ether. These results indicate that the composition of this invention exhibits a higher inhibitory effect on lateral buds than conventional inhibitors in the greenhouse pot test and field test. Whereas the use of auxiliary agents is liable to cause phytotoxicity with conventional inhibitors, these tests also revealed that the present composition produced no phytotoxicity or reduced phytotoxicity only.

Thus the compositions of this invention enable HP or salt thereof to spread on and penetrate into plants to a greatly increased extent and to thereafter promptly migrate into the meristematic tissue within the plant body, producing a remarkably enhanced growth inhibiting activity with high stability even under a wide variety of weather conditions without being influenced by the environmental factors. The present compositions are therefore very useful as plant growth inhibitors.

EXAMPLE 1

Ten seeds of oats are sown in each of polyvinyl chloride pots, 12 cm in diameter, and germinated in a greenhouse (28° C., 78% RH). On the 7th day after the sowing, the length of each second leaf is measured. Each of the Compositions No. 1 to No. 7 of this invention listed in Table 1 is diluted 100-fold with water, and the solution is applied to the seedlings of three pots in an amount of 10 ml per pot. On the 14th day after the sowing, the elongation of the second leaf is measured. Based on comparison with a nontreated control group, the growth inhibition ratio (I.R.) is calculated from Equation (I) below. For comparison, the same procedure as above is repeated with the use of Comparison Compositions No. 1 to 6 listed in Table 1.

$$I.R. = (1 - Mn/Mo) \times 100 \ (\%)$$

where Mo is the elongation of the second leaf in the control group, and Mn is that in the treated grop.

The results are given in Table 2 which also shows the cloud points of the compositions.

Table 1

| Composition No. | HP salt (Amount, %) | Compound of formula (A) (Amount, %) | Compound of formula (B) (Amount, %) |
|---|---|---|---|
| This invention | | | |
| 1 | Potassium salt of HP (18.0%) | Polyoxyethylene(9)nonylphenyl ether (5%) | Sodium sulfate of polyoxyethylene(75)nonylphenyl ether (3%) |
| 2 | Potassium salt of HP (18.0%) | Polyoxyethylene(11)nonylphenyl ether (9%) | Sodium sulfate of polyoxyethylene(75)nonyl phenyl ether (3%) |
| 3 | Potassium salt of HP (18.0%) | Polyoxyethylene(8)lauryl ether (2%) | Sodium sulfate of polyoxyethylene(50)lauryl ether (2%) |
| 4 | Potassium salt of HP (18.0%) | Polyoxyethylene(10)trimethylnonyl ether (9%) | Sodium sulfate of polyoxyethylene(75)nonylphenyl ether (3%) |
| 5 | Diethanolamine salt of HP (18.0%) | Polyoxyethylene(9)nonylphenyl ether (2%) | Sodium sulfate of polyoxyethylene(4)nonylphenyl ether (5%) |
| 6 | Lysine salt of HP (18.0%) | Polyoxyethylene(9)nonylphenyl ether (2%) | Sodium sulfate of polyoxyethylene(4)nonylphenyl ether (5%) |
| 7 | Choline salt of HP (18.0%) | Polyoxyethylene(9)nonylphenyl ether (2%) | Sodium sulfate of polyoxyethylene(4)nonylphenyl ether (5%) |
| Comparison | | | |
| 1 | Potassium salt of HP (18.0%) | Polyoxyethylene(11)nonylphenyl ether (12%) | None |
| 2 | Potassium salt of HP (18.0%) | None | Sodium sulfate of polyoxyethylene(75)nonylphenyl ether (12%) |
| 3 | Potassium salt of HP (18.0%) | None | None |
| 4 | Diethanolamine salt of HP (30.0%) | None | None |
| 5 | Potassium salt of HP (18.0%) | Polyoxyethylene(10)trimethylnonyl ether (12%) | None |
| 6 | Potassium salt of HP (18.0%) | Polyoxyethylene(11)nonylphenyl ether (9%) | Sodium dioctylsulfosuccinate*1 (3%) |

*1: Sodium dioctylsulfosuccinate is not included in compounds of Formulae A and B.

Table 2

| Composition No. | Growth inhibiting effect on oats I.R. % | Cloud point °C. |
|---|---|---|
| This Invention | | |
| 1 | 93.8 | 65 (20) |
| 2 | 93.0 | 70 (46) |
| 3 | 85.0 | 75 (20>) |
| 4 | 93.3 | 65 (47) |
| 5 | 95.5 | 100 (20>) |
| 6 | 96.0 | 90 (20>) |
| 7 | 92.1 | 100 (20>) |

Table 2-continued

| Composition No. | Growth inhibiting effect on oats I.R. % | Cloud point °C. |
|---|---|---|
| Comparison | | |
| 1 | 70.0 | 47 |
| 2 | 65.0 | — |
| 3 | 5.2 | — |
| 4 | 68.3 | — |
| 5 | 65.3 | 47 |
| 6 | 65.8 | 47 |

Note:
The values in the parentheses are the cloud points of the compositions not containing the compound of the formula (B).

EXAMPLE 2

Each of Compositions No. 1 to No. 7 according to this invention and Comparison Compositions No. 1 to 6 (except for No. 3) used in Example 1 is tested for activity to inhibit the growth of lateral buds on tobacco in the field. The composition is diluted 60-fold with water, and the solution is applied by a semi-automatic sprayer of the shouldering type to tobacco plants in an amount of 20 ml per tobacco plant. On the 14th day after the application, the lateral buds on the uppermost three joints of each plant are collected, and the total weight of the lateral buds per plant is determined. Each of the compositions is tested on three groups of tobacco each including 50 plants. The results are given in Table 3 in which the weight of lateral buds in each group is the average of 50 plants.

Table 3

| Composition No. | Weight of lateral buds (g/plant) | | | |
|---|---|---|---|---|
| | Group A | Group B | Group C | Average of A, B and C |
| This Invention | | | | |
| 1 | 1.0 | 0.6 | 0.9 | 0.8 |
| 2 | 1.5 | 1.3 | 0.7 | 1.2 |
| 3 | 2.0 | 2.0 | 1.5 | 1.8 |
| 4 | 1.3 | 1.5 | 1.8 | 1.5 |
| 5 | 1.0 | 0.7 | 0.5 | 0.7 |
| 6 | 0.8 | 0.4 | 0.8 | 0.7 |
| 7 | 1.2 | 1.0 | 0.9 | 1.0 |
| Comparison | | | | |
| 1 | 4.9 | 3.6 | 3.5 | 4.0 |
| 2 | 3.8 | 5.1 | 6.7 | 5.2 |
| 4 | 1.5 | 3.2 | 2.8 | 2.5 |
| 5 | 5.7 | 5.0 | 6.7 | 5.8 |
| 6 | 6.7 | 6.0 | 6.0 | 6.2 |

EXAMPLE 3

Each of Compositions No. 1–6 shown in Table 4 is tested for activity to inhibit the growth of lateral buds on tobacco in the field by the same manner as in Example 2. The results are given in Table 5 in which the weight of lateral buds in each group is the average of 50 plants.

Table 4

| Composition No. | Ingredient | | |
|---|---|---|---|
| | HP salt (Amount, %) | Compound of formula (A) (Amount, %) | Compound of formula (B) (Amount, %) |
| This Invention | | | |
| 1 | Potassium salt of HP (18.0%) | Polyoxyethylene(10)octyl-naphthyl ether (8%) | Polyoxyethylene(25)tri-decylphenyl ether sodium sulfate (5%) |
| 2 | Potassium salt of HP (18.0%) | Polyoxyethylene(10)octyl-naphthyl ether (5%) | Polyoxyethylene(25)octyl-naphthyl ether sodium sulfate (5%) |
| 3 | Potassium salt of HP (18.0%) | Polyoxyethylene(10)octyl-naphthyl ether (3%) | Polyoxypropylene(25)lauryl-naphthyl ether sodium sulfate (6%) |
| Comparison | | | |
| 4 | Potassium salt of HP (18.0%) | Polyoxyethylene(11)nonyl-phenyl ether (12%) | none |
| 5 | " | none | Polyoxyethylene(75)nonyl-phenyl ether sodium sulfate |
| 6 | " | none | none |

Table 5

| Composition No. | Weight of lateral buds (g/plant) | | | |
|---|---|---|---|---|
| | Group A | Group B | Group C | Average of A, B and C |
| This Invention | | | | |
| 1 | 0.8 | 0.9 | 1.1 | 0.9 |
| 2 | 0.9 | 1.1 | 1.2 | 1.1 |
| 3 | 1.1 | 1.2 | 1.3 | 1.2 |
| Comparison | | | | |
| 4 | 1.5 | 3.2 | 2.8 | 2.5 |
| 5 | 5.7 | 5.0 | 6.7 | 5.8 |
| 6 | 6.7 | 6.0 | 6.0 | 6.2 |

What we claim is:

1. A composition for inhibiting the growth of plants comprising:
   (1) 6-hydroxy-3-(2H)-pyridazinone or a salt thereof, said salt being at least one species selected from the group consisting of potassium, sodium, ethanolamine, diethanolamine and triethanolamine salts of 6-hydroxy-3-(2H)-pyridazinone,
   (2) at least one compound represented by the formula:

$$R^1-O-[CH_2CH(R^2)-O]_l-H \qquad (A)$$

wherein $R^1$ is an alkyl group having 6 to 12 carbon atoms, an alkenyl group having 6 to 12 carbon atoms, an aralkyl group having 6 to 12 carbon atoms, an alkylphenyl group having a $C_6$–$C_{15}$-alkyl group, or an alkylnaphthyl group having a $C_8$–$C_{18}$-alkyl group; $R^2$ is H or $CH_3$; and $l$ is an integer of 3 to 30; and
   (3) at least one compound represented by the formula:

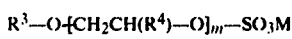

wherein $R^3$ is an alkyl group having 6 to 12 carbon atoms, an alkenyl group having 6 to 12 carbon atoms, an aralkyl group having 6 to 12 carbon atoms, an alkylphenyl group having a $C_6$-$C_{15}$-alkyl group or an alkylnaphthyl group having a $C_8$-$C_{18}$-alkyl group; $R^4$ is H or $CH_3$; m is an integer of 1 to 100; and M is an alkali metal, an ammonium group, a quaternary ammonium group or H;

said composition containing a plant growth inhibiting amount of 6-hydroxy-3-(2H)-pyridazinone or a salt thereof, 0.001 to 1.5 parts by weight of the compound represented by the formula (A) per part by weight of the pyridazinone or salt thereof and 20 to 500% by weight of the compound represented by the formula (B) based on the compound represented by the formula (A).

2. A composition as defined in claim 1 wherein the compound represented by the formula (A) is a polyoxyethylenenonylphenyl ether or polyoxyethyleneoctylphenyl ether having 6 to 20 oxyethylene chains.

3. A composition as defined in claim 1 wherein the compound represented by the formula (B) is sodium sulfate of a polyoxyethylenenonylphenyl ether having 1 to 100 oxyethylene chains.

4. A composition as defined in claim 1 wherein the concentration of at least one of 6-hydroxy-3-(2H)-pyridazinone and salts thereof is 0.1 to 1%.

5. A composition as defined in claim 1 wherein the concentration of the compound represented by the formula (A) is not lower than the critical micelle concentration thereof.

6. A composition as defined in claim 1 wherein 0.03 to 1 part by weight of the compound represented by the formula (A) is contained per part by weight of the 6-hydroxy-3-(2H)-pyridazinone or salt thereof.

* * * * *